United States Patent [19]

Haindl

[11] Patent Number: 5,306,255
[45] Date of Patent: Apr. 26, 1994

[54] PORTCATHETER

[76] Inventor: Hans Haindl, Hauptstr. 39, 3015 Wennigsen 1, Fed. Rep. of Germany

[21] Appl. No.: 940,018

[22] Filed: Sep. 3, 1992

[30] Foreign Application Priority Data

Sep. 7, 1991 [DE] Fed. Rep. of Germany ....... 4129782

[51] Int. Cl.⁵ .............................................. A61M 5/32
[52] U.S. Cl. .................................. 604/175; 604/891.1
[58] Field of Search .................. 604/175, 126, 891.1; 128/DIG. 12

[56] References Cited

U.S. PATENT DOCUMENTS

| 4,784,646 | 11/1988 | Feingold | 604/175 |
| 4,904,241 | 2/1990 | Bark | 604/175 |
| 4,929,236 | 5/1990 | Sampson | 604/175 |
| 5,006,115 | 4/1991 | McDonald | 604/175 |
| 5,137,529 | 8/1992 | Watson et al. | 604/175 |

FOREIGN PATENT DOCUMENTS 134745  3/1985  European Pat. Off. ............ 604/175

Primary Examiner—John G. Weiss
Attorney, Agent, or Firm—Allegretti & Witcoff

[57] ABSTRACT

A subcutaneous portcatheter for injecting fluid into a patient through a catheter tube. The tube connects to a generally flat housing having a central chamber surrounded by an annular chamber containing a band filter. A soft needle-pierceable cover overlies the chambers. The central chamber connects to the annular chamber through a hole in the circular wall separating the two chambers, the hole being located diametrically opposite the outlet to the catheter tube. Fluid injected through the cover into the central chamber flows through the hole, through the filter, into the annular chamber outside the filter, exiting the housing through the outlet to the catheter tube.

9 Claims, 1 Drawing Sheet

U.S. Patent
Apr. 26, 1994
5,306,255
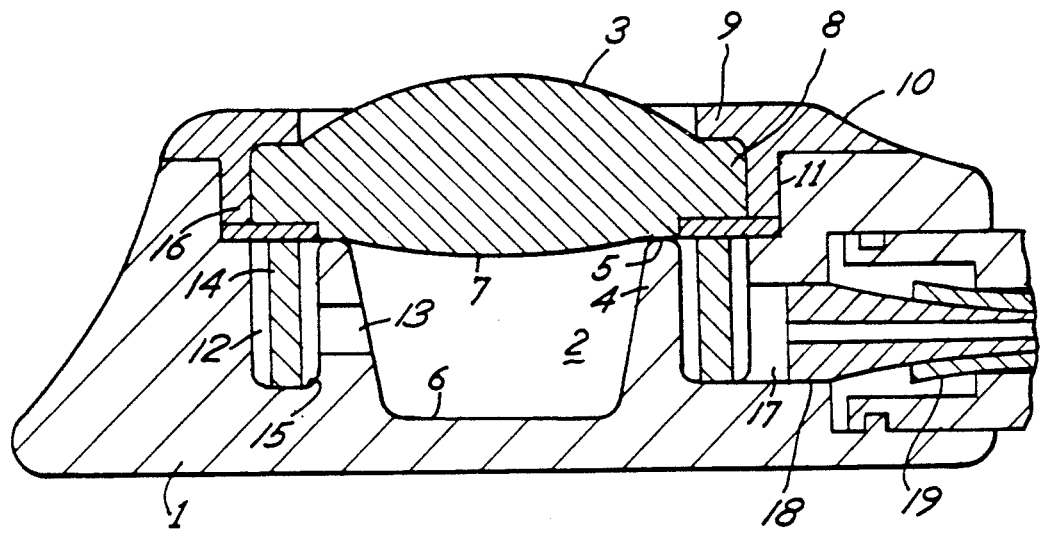
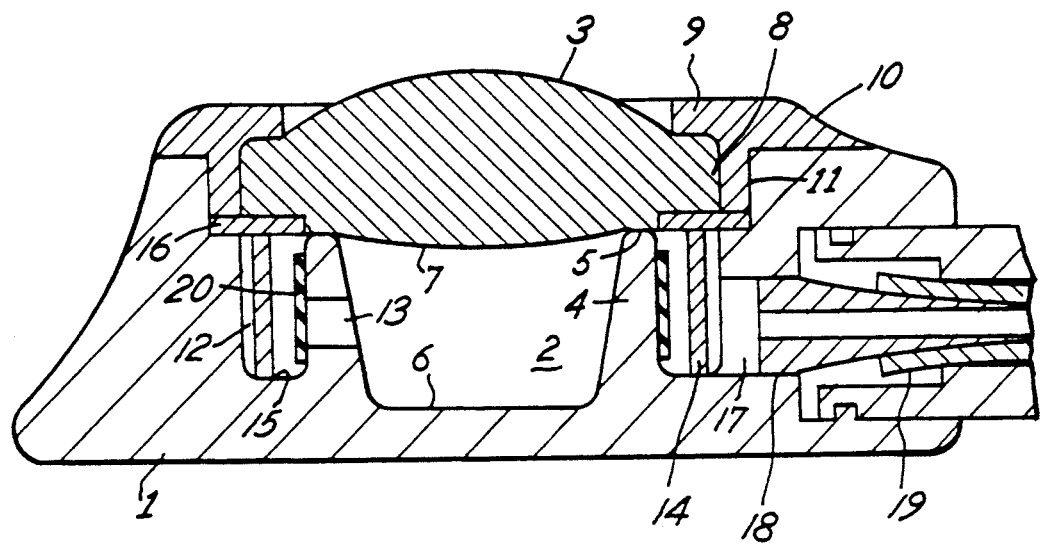

PORTCATHETER

BACKGROUND OF THE INVENTION

The invention refers to a portcatheter for injecting, through a catheter, medication into a vessel within the body from a point outside the body.

PRIOR ART

Portcatheters of the described type are implanted in the body to facilitate the access to blood vessels and other body cavities that are otherwise not accessible from outside. A capsule that lies below the skin has a cover that can be punctured by a needle piercing the skin. From this capsule, the injected drug is delivered to the body cavity through the catheter.

A disadvantage of the known port catheters is that particles may be formed by punching the covering of the capsule and become entrained in injected liquid. Especially, in portcatheters that are fitted with very small lumen catheters these particles can block the tubing. Another disadvantage of prior catheters is that blood may enter the catheter or even the inner chamber of the portcatheter. This may cause a thrombotic blockage of the tubing. To avoid this, a valve is placed at the free end of the catheter tubing, but this solution is complicated and thickens the end of the tubing.

To prevent particles from blocking the catheter tubing, a portcatheter sold under the name "Periplant" (manufactured by B. Braun in Melsungen/Germany) has a sintered metal filter formed like a pot inside of the housing. The bottom of the potlike filter is without function. The work required of this filter is great. Additionally, the injected fluid will flow through the shortest distance to the catheter tubing. For this reason, some areas of the filter are not perfused. In these areas, bacteria will grow because they are not being flushed.

In another portcatheter, a metallic tissue inside of the chamber performs as a filter. This tissue can be punctured by the cannula and be destroyed, so that the filter will not function.

U.S. Pat. No. 4,784,646 discloses a catheter having a first and a second chamber aligned with each other in the direction of the puncture. The chambers are separated by a metallic sieve. Behind this sieve in direction of the puncture there is a filter of porous foam. The sieve, as well as the filter, are constructed as plugs that are pressed into the conical inner wall of the housing. The metallic sieve is designed to prevent entry of foam particles from the filter into the second chamber, which particles might cause a blockage of the catheter.

This known portcatheter has the disadvantage that the height of the body in the direction of the puncture, that is vertically to the skin surface of a patient, must be relatively large because the two chambers are disposed on top of each other. Another disadvantage is that the metallic sieve and the associated filter are fixed inside the housing mainly by friction. To assemble them, a special tool is necessary. During assembly, the metallic filter can cause filings that may later lodge in the catheter. Besides that, there is the danger that the metallic sieve will be loosened and dislocated by the forces of the injection needles so that there is no separation between the two chamber. Similarly, the filter might be dislocated by the hydraulic pressure of the injection.

EP O 347 743 A2 shows a portcatheter or implantable pump that consists of two chambers. One of the chambers is connected with a ring groove in the surface of the portcatheter that is covered by a ring shaped membrane of a material that is pierceable by an injection needle. The two chambers are separated by a flexible membrane. The chamber, not in connection with the pierceable covering, contains a volatile driving agent that expands by the temperature of the body and produces pressure on the membrane. The pressure forces the drug in the other chamber to be slowly discharged to the patient. There are no means to prevent the passage of particles.

U.S. Pat. No. 4,405,320 shows an implantable tubelike body that is essentially T-shaped. The top part of the T is implanted in a blood vessel; the 90° part contains a membrane of soft material with slits lying tight on one another. The slits are covered by a mask with holes that permit a needle to penetrate the slits. There are no means to prevent the passage of particles.

THE INVENTION

The object of the invention is to construct a portcatheter that prevents particles from passing to the catheter or to the blood vessel and that also prevents the backflow of blood through the catheter to the port chamber, which is simply constructed and safe in function.

SUMMARY OF THE INVENTION

The basic idea is to fit the fluid housing with an additional cavity containing a filter or a valve, and through which the injected drug will flow. This cavity is annular, to provide a large flow area around the central opening and to permit the use of a simple ring type filter. Additionally or alternatively, this housing may include a valve to prevent the backflow of blood from the catheter.

According to a further feature of the invention, a hole is provided in the wall between the central chamber of the housing and the surrounding annular cavity, located diametrically opposite the channel leading to the catheter tube. By this means, flow through all parts of the filter is assured, and especially, through the annular cavity. No part of the central chamber is not flushed by the injected drug.

The valve in the annular cavity may be formed simply by an elastic band that is preferably made of silicone elastomer and that embraces the circular wall of the cavity and covers the hole through this wall. Injecting a drug into the chamber of the housing causes the elastic band to lift from the wall and permit the drug to pass through the hole. A backflow, and especially a backflow of blood into the catheter tubing, is prevented because a current in the other direction will press the band against the wall surrounding the hole and close it tightly.

The filter housed in the annular cavity is ring shaped and fixed between the bottom of the annular cavity and the covering. That means a simple assembly and a tight fit between the filter and the neighboring parts.

To prevent the puncturing needle from damaging the filter, or from entering the annular cavity it is advantageous to have a hard non-pierceable washer between the annular cavity and the covering.

DETAILED DESCRIPTION

The drawing shows two embodiments of the invention.

FIG. 1 is a vertical sectional view of a portcatheter according to the invention with partly-shown catheter tubing and mounted filter.

FIG. 2 is a view similar to FIG. 1 which shows a valve between the central and annular chambers.

The portcatheter shown in cross-section in FIG. 1 consists of a generally flat housing 1 with a central blind opening of chamber 2 closed by a cover 3 made of soft material pierceable by an injection needle. The chamber 2 is formed by a circular wall 4 that extends axially from the bottom 6 of the housing 1. The free edge or rim 5 of the wall 4 is in contact with the lower surface 7 of the cover 3.

The cover 3 with its circumferential margin 8 is squeezed into a circumferential recess in the inner side wall of the housing 1 above the free edge 5 of the circular wall 4. Preferably, an insert 10, is pressed into a countersink 11 in the housing 1. Insert 10 has a circumferential flange 9 to secure cover 3. This construction permits insertion of a washer as explained below.

Outside the circular wall 4 is an annular cavity 12 that is concentric with the chamber 2 and connected with chamber 2 through a hole 13 in the wall. A ring shaped band filter 14 extends from the bottom 15 of the annular cavity 12 to a hard non-pierceable washer 16 that covers the open end of the chamber 12 to prevent an injection needle from damaging the filter 14 or injecting the fluid outside the filter 14. The washer 16 is held under the margin 8 of the cover 3.

Diametrically opposite the hole 13 a radial channel 17 in the housing connects annular cavity 12 to a connecting tube 18 which in turn is connected with the catheter tubing 19 (only partly shown).

The portcatheter shown in FIG. 1 is implanted just beneath the patient's skin. The catheter tube 19 is connected with a vessel or a body cavity. If a drug is to be administered to the vessel or the cavity, an injection needle is punctured through the skin and the cover 3 and the drug is injected into the chamber 2. It flows through the hole 13 in the part of the annular chamber 12 that lies inside the filter 14, passes through the filter 14 leaving particles on the filter and then flows around the outside of the filter 14 in the annular space 12 to the diametrically opposite channel 17, and then into the catheter tube 19 and the vessel or cavity.

FIG. 2 shows a variation of the portcatheter of FIG. 1. Same or equal parts are designated with the same numbers. The difference lies in the fact that a band 20 of silicone elastomer is stretched over the outer face of wall 4 covering hole 13. When the drug injected into the chamber 2, the elastic band 20 is lifted by the hydraulic pressure from the margin of wall 4 surrounding hole 13 so that the drug is able to flow into the annular chamber 12 where additionally a filter 14 like the one in FIG. 1 mounted. From the annular chamber 12, the drug flows, as in the construction of FIG. 1, to the catheter tube 19 and the adjacent vessel or body cavity. Flow in the opposite direction is inhibited by check valve function provided by the elastic band 20 and the hole 13 so that no blood may enter the catheter tubing and block it.

I claim:

1. A portcatheter comprising
a generally flat housing,
a central blind opening within said housing formed by a circular wall extending axially from the bottom of said housing, said circular wall terminating in a free edge,
an annular cavity outside said circular wall concentric with said circular wall,
a soft, needle-pierceable cover disposed within said opening, lying tightly on the free edge of said wall, said cover having a circumferential margin
said circumferential margin overlying said annular cavity,
a hole through said wall connecting said central blind opening to said annular cavity,
a check valve for said hole which permits fluid flow in one direction from said opening to said annular cavity, and
a catheter tube communicating with said annular chamber.

2. The portcatheter of claim 1 in which said check valve comprises an elastic band embracing said circular wall and covering said hole.

3. A portcatheter comprising
a generally flat housing having a central opening in the top thereof,
a central chamber within said housing formed by a circular wall extending axially from the bottom of said housing, said circular wall terminating in a free edge,
an annular cavity outside said circular wall concentric with said chamber,
a soft, needle-pierceable cover disposed within said opening, lying tightly on the free edge of said wall, said cover having a circumferential margin,
said circumferential margin overlying said annular cavity,
a hole through said wall connecting said chamber to said annular cavity,
a ring shaped filter disposed in said annular cavity and
a catheter tube communicating with said annular cavity.

4. The portcatheter of claim 3 in which said hole is located diametrically opposite said catheter tube.

5. The portcatheter of claim 3 which includes a check valve for said hole, said valve comprising an elastic band embracing said circular wall and covering said hole.

6. The portcatheter of claim 5 in which said elastic band is made of silicone elastomer.

7. The portcatheter of claim 3 in which said ring shaped filter extends vertically between the bottom of said annular cavity and said cover.

8. The portcatheter of claim 3 in which includes a hard washer disposed between said annular cavity and said cover to protect said filter.

9. The portcatheter of claim 4 in which said housing has a circular shoulder surrounding said annular cavity on which said hard washer is supported.

* * * * *